(12) United States Patent
Jacob et al.

(10) Patent No.: US 8,211,252 B2
(45) Date of Patent: Jul. 3, 2012

(54) FURAZANE DERIVATIVES, PREPARATION THEREOF AND ENERGETIC COMPOSITIONS CONTAINING THEM

(75) Inventors: Guy Jacob, Vert-le-Petit (FR); Gregoire Herve, Verberie (FR); Guy Cagnon, Ballancourt (FR); Frederic Alvarez, Salaise sur Sanne (FR)

(73) Assignee: Eurenco, Paris (FR)

( * ) Notice: Subject to any disclaimer, the term of this patent is extended or adjusted under 35 U.S.C. 154(b) by 376 days.

(21) Appl. No.: 12/521,680

(22) PCT Filed: Jan. 15, 2008

(86) PCT No.: PCT/FR2008/050066
§ 371 (c)(1),
(2), (4) Date: Jun. 29, 2009

(87) PCT Pub. No.: WO2008/102092
PCT Pub. Date: Aug. 28, 2008

(65) Prior Publication Data
US 2010/0132856 A1    Jun. 3, 2010

(30) Foreign Application Priority Data
Jan. 16, 2007  (FR) ...................... 07 52689

(51) Int. Cl.
*C06B 25/00* (2006.01)
*C06B 25/34* (2006.01)
*D03D 23/00* (2006.01)
*D03D 43/00* (2006.01)

(52) U.S. Cl. ............... 149/92; 149/88; 149/109.4
(58) Field of Classification Search .......... 149/92, 149/88, 109.4
See application file for complete search history.

(56) References Cited

U.S. PATENT DOCUMENTS

5,071,495 A * 12/1991 Willer et al. .............. 149/19.9
5,747,729 A * 5/1998 Chassaing et al. ......... 149/19.1
6,388,087 B1 * 5/2002 Bashir-Hashemi et al. .. 548/125

FOREIGN PATENT DOCUMENTS

EP  0 816 306 A1  1/1998
FR  2 750 421 A1  1/1998
RU  2 248 354 C1  3/2005

OTHER PUBLICATIONS

Batog, L. et al. "Triazolyl-1,2,5-Oxadiazoles—New Class of Energetic Compounds", Database CA Chemical Abstracts Service, XP002454200, 30$^{th}$ International Annual Conference of ICT, Jun. 29-Jul. 2, 1999.
Sheremetev, A. et al. "Synthesis of Difurazanyl Ethers from 4,4'-Dinitroazoxyfurazan", Heteroatom Chemistry, vol. 11, No. 1, 2000, pp. 48-56.
Novikova, T. et al. "An Effective Method for the Oxidation of Aminofurazans to Nitrofurazans", Mendeleev Commun., 1994, pp. 138-140.
Sheremetev, A., et al. "An efficient synthesis of Hydroxyfurazans", Mendeleev Coummun. 1998, pp. 238-239.
Licht, H. et al. "New Energetic Materials From Triazoles and Tetrazines", Journal of Energetic Materials, vol. 12, 1994, pp. 223-235.
Batog, L. et al. "Synthesis of (1,2,3-Triazol-1-YL)Furazans. 2*.Reaction of Azidofurazans With Morpholinonitroethene", Chemistry of Heterocyclic Compounds, vol. 36, No. 3, 2000, pp. 343-345.
Sheremetev, A. et al. "Transetherification of difurazanyl ethers as a route to unsymmetrical derivatives of difurazanyl ether", Russian Chemical Bulletin, International Edition, vol. 51, No. 4, Apr. 2002, pp. 659-662.
Batog, L. et al. "Synthesis of nitro, nitroso, azo, and asido derivatives of (4-R$^1$-5-R$^2$-1,2,3-triazol-1-yl)-1,2,5-oxadiazoles by oxidation and diazotization of the corresponding amines", Russian Chemical Bulletin, International Edition, vol. 54, No. 8, Aug. 2005, pp. 1915-1922.
Rozhkov, V. et al. "Nucleophilic substitution in the series of (1,2,3-triazol-1-yl)-1,2,5-oaxdiazoles. Reactions with N-, O-, and S-nucleophiles", Russian Chemical Bulletin, International Edition, vol. 54, No. 8, Aug. 2005, pp. 1923-1934.
Sheremetev, A. et al. "(Pyrrol-1-yl)furazans", Russian Chemical Bulletin, International Edition, vol. 52, No. 6, Jun. 2003, pp. 1413-1418.
Database CA Chemical Abstracts Service, Batog, L et al. "Triazolyl-1,2,5-oxadiazoles. New Class of energetic compounds", XP002454200, 1999.

Gunasekaran, A. et al. "A Convenient Synthesis of Diaminoglyoxime and Diaminofurazan: Useful Precursors for the Synthesis of High Density Energetic Materials", Journal of Heterocyclic Chemistry, vol. 32, No. 4, 1995, pp. 1405-1407.
Gunasekaran, A. et al. "Dense Energetic Compounds of C, H, N, and O Atoms. III. 5-[4-Nitro-(1,2,5)oxadiazolyl]-5H-[1,2,3]triazolo[4,5-c][1,2,5]oxadiazole", Heteroatom Chemistry, vol. 4, No. 5, 1993, pp. 521-524.
Database CA Chemical Abstracts Service, Sheremetev, A. et al. "Furazan derivatives: high energetic materials from diaminofurazan", XP002454201, 2004.
Database CA Chemical Abstracts Service, Lempert, D. et al. "Dependence of the specific impulse composite propellants containing oxidizing agents based on C, N, and O atoms", XP002454202, 2004.

\* cited by examiner

*Primary Examiner* — James McDonough
(74) *Attorney, Agent, or Firm* — Hamre, Schumann, Mueller & Larson, P.C.

(57) ABSTRACT

A subject matter of the present invention is:
the compounds of formula (I):

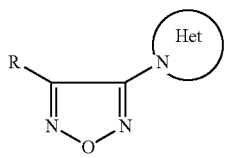

(I)

in which:

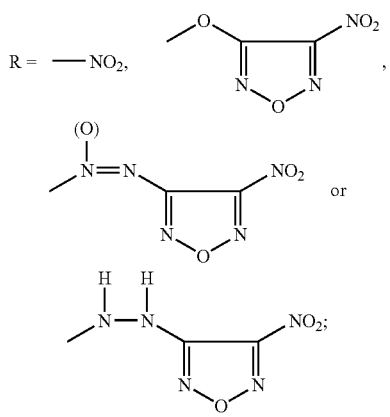

and Het is an azolyl radical: nitroazolyl or tetrazolyl; with the exception of 3-nitro-4-(4-nitro-1,2,3-triazol-1-yl)furazan;

the preparation of said compounds; and the energetic compositions including at least one compound chosen from said compounds of formula (I) and 3-nitro-4-(4-nitro-1,2,3-triazol-1-yl)furazan.

8 Claims, 1 Drawing Sheet

FURAZANE DERIVATIVES, PREPARATION THEREOF AND ENERGETIC COMPOSITIONS CONTAINING THEM

A subject matter of the present invention is:
novel heterocyclic molecules: novel compounds, derived from furazan, resulting from coupling between a furazan and an azole;
the preparation of said novel molecules; and
novel energetic compositions.

These novel compounds (these novel molecules) are particularly advantageous in that they are simultaneously highly energetic and of reduced vulnerability; in that they correspond particularly advantageously to the following specifications:
high energetic performance characteristics,
low sensitivity, and
high thermal stability.

Furazans constitute a family of nitrogenous heterocycles having high enthalpies of formation by virtue of a high aromatic ring energy. Their energy potential and their high thermal stability make them advantageous and promising molecules in the field of energetic materials.

A first document, U.S. Pat. No. 5,071,495, described in 1991 the use of furazans of diaminofurazan (DAF) type in aluminized propellants comprising ammonium perchlorate. Said furazans are used at low charge levels and the propellants concerned show relatively poor performance characteristics.

The document RU 2 248 354 subsequently described the synthesis of a furazan of high molecular weight (molar mass=420 g/mol) which is thermally stable (decomposition temperature: 267° C.) and which can be used in explosives capable of operating at relatively high temperatures, inside drilling wells. The performance characteristics stated in this document are once again poor (detonation velocity: 8090 km/s).

Chassaing and Finck, in application FR 2 750 421, described the use of charges of dinitrobifurazan type exhibiting higher energy levels. Nevertheless, these compounds exhibit certain disadvantages, in particular chemical instabilities and incompatibilities with the binders and additives present in propellants and explosives. Sheremetev et al. in fact showed, in *Heteroatom. Chemistry*, 2000, 11, 48, that dinitroazoxyfurazan could be cleaved at the azoxy bridge or at the carbon carrying one of the two nitro groups in the presence of nucleophiles, such as alcohols. These reactions take place rapidly at ambient temperature.

One publication (International Annual Conference of ICT (1999), 30th, 57/1-57/11) has mentioned 4-nitro-3-(4,5-dinitro-1H-1,2,3-triazol-1-yl)-1,2,5-oxadiazole. It does not describe the preparation of this compound. It simply presents predictive calculations of performance with regard to this hypothetical chemical structure.

Another publication (Russian Chemical Bulletin, International Edition, Vol. 52, No. 6, pp. 1413-1418 (June, 2003)) has described the synthesis of (pyrrol-1-yl)furazans. The pyrrole heterocycle of said furazans is not substituted.

Two chemical publications (Russian Chemical Bulletin, International Edition, Vol. 54, No. 8, pp. 1915-1922 and pp. 1923-1934 (August 2005)) have as subject the synthesis of (1,2,3-triazol-1-yl)-1,2,5-oxadiazole derivatives. They describe, as chemical product, 3-nitro-4-(4-nitro-1,2,3-triazol-1-yl)furazan.

A person skilled in the art is always looking for novel energetic compounds exhibiting an advantageous compromise in terms of performance characteristics, vulnerability and thermal stability. To date, no document reports high performance uses of furazans in the fields of propulsion and explosives. Furthermore, a person skilled in the art has often blamed furazans for their very high sensitivity to impacts and to friction.

The inventors have surprisingly identified a novel class of furazans which are particularly effective with reference to the specifications or compromise indicated above.

Said novel furazans constitute the first subject matter of the present invention. They correspond to the formula (I) below:

in which:

and Het is an azolyl radical chosen from nitroazolyl and tetrazolyl radicals; and are other than 3-nitro-4-(4-nitro-1,2, 3-triazol-1-yl)furazan (see above).

Said novel furazans are monofurazans (R=—NO$_2$) or bifurazans (R=the other 4 radicals identified above).

Het is an azolyl radical, that is to say "deriving" from a 5-membered nitrogenous heterocycle, at least one nitrogen of which is bonded to a hydrogen atom. Het is an azolyl radical chosen from nitroazolyl radicals (azolyl radicals substituted by at least one nitro group) and tetrazolyl radicals (unsubstituted tetrazolyl radicals).

Het generally includes a single heterocycle (5-membered) or two heterocycles (5-membered) bonded via a C—C bond. Advantageously, Het is chosen from:
unsubstituted tetrazolyl and bitetrazolyl ((bi)tetrazolyl) radicals;
pyrrolyl and bipyrrolyl ((bi)pyrrolyl) radicals substituted by at least one nitro group;
pyrazolyl and bipyrazolyl ((bi)pyrazolyl) radicals substituted by at least one nitro group;
triazolyl and bitriazolyl ((bi)triazolyl) radicals substituted by at least one nitro group (said radicals and particularly the triazolyl radicals are very advantageously substituted by just one nitro group); and
tetrazolyl and bitetrazolyl ((bi)tetrazolyl) radicals substituted by at least one nitro group.

Het can in particular be chosen from the nitrotriazolyl (in particular nitro-1,2,3-triazolyl and nitro-1,2,4-triazolyl); dinitrotriazolyl; dinitropyrazolyl(3,4-dinitropyrazolyl and 3,5-dinitropyrazolyl); tetrazolyl; 5-nitrotetrazolyl; poly(nitropyrrolyl) (more particularly bi(nitropyrrolyl)); bitetrazolyl; bi(nitrotriazolyl) and bi(dinitropyrazolyl) radicals.

Het is advantageously chosen from the following radicals:
3-nitro-1,2,4-triazol-1-yl,
4-nitro-1,2,3-triazol-2-yl,
4-nitro-1,2,3-triazol-1-yl,
3,4-dinitropyrazolyl,
3,5-dinitropyrazolyl,
1,2,3,4-tetrazol-1-yl.

In the context of its first subject matter, the present invention encompasses the novel compounds of the formula (I) identified below:
3-nitro-4-(3-nitro-1,2,4-triazol-1-yl)furazan,
3-nitro-4-(4-nitro-1,2,3-triazol-2-yl)furazan,
4-nitro-4'-(4-nitro-1,2,3-triazol-2-yl)bisfurazanyl ether,
4-nitro-4'-(4-nitro-1,2,3-triazol-1-yl)-3,3'-azoxybisfurazan,
3-nitro-4-(3,4-dinitropyrazolyl)furazan,
3-nitro-4-(3,5-dinitropyrazolyl)furazan.

According to its second subject matter, the present invention relates to the preparation of said novel compounds of the formula (I).

Generally and in an entirely novel fashion, said novel compounds can be obtained by coupling
a nitrofurazan of formula (IIa)

in which R is as defined above with reference to the formula (I), and
an azole of formula (IIb)

in which Het is as defined above in reference to the formula (I).

Said coupling results from a nucleophilic substitution of a mono- or bifurazan (of formula (IIa), carrying a leaving group of nitro type) by an azole of formula (IIb).

The reaction is carried out in the presence of an organic or inorganic base in a polar organic solvent, preferably an anhydrous polar organic solvent. The solvent used can be chosen in particular from acetone, tetrahydrofuran, dimethylformamide, dimethyl sulfoxide, acetonitrile, nitromethane, sulfolane and their mixtures. Said reaction can be carried out at a temperature between ambient temperature and the reflux temperature of the solvent used. Preferably, the coupling is carried out in acetonitrile at ambient temperature.

The nucleophilic substitution concerned is thus carried out on a nitrofurazan of the formula (IIa), which acts as electrophile, chosen from:
a) dinitrofurazan,
b) dinitrofurazanyl ether,
c) dinitroazofurazan,
d) dinitroazoxyfurazan, and
e) dinitrohydrazofurazan.

These compounds (monofurazan for compound a), bifurazans for compounds b) to e)) are described in the literature. Compounds a) to d) have in particular been described by:

A. B. Sheremetev et al. in *Mendeleev Commun.* 1994, 138-140; or

A. B. Sheremetev et al. in *Mendeleev Commun.* 1998, 238. Compound e) has for its part been described in particular in U.S. Pat. No. 6,388,087.

There are many azoles (of formula (IIb)) capable of acting as nucleophile. They can in particular consist of the azoles corresponding to the azolyl radicals specified above. Said azoles are compounds known per se.

The coupling method specified above is suitable for the preparation of all the compounds of the invention. It is exemplified in examples 1, 2, 6 and 7 below.

However, some of the compounds of the invention can be obtained, under more advantageous conditions, by other methods. The intention is to specify such other, more selective, methods below.

Advantageously, it is thus possible to prepare (more selectively) the subfamily of the compounds of formula (I) in which Het is the 1,2,3,4-tetrazol-1-yl radical; or the 5-nitro-1,2,3-triazol-2-yl radical; or the 4-nitro-1,2,3-triazol-1-yl radical, according to other methods carried out starting from an aminofurazan of formula (IIIa):

in which R is as defined above.

For the preparation of a compound of formula (I) in which Het is a tetrazolyl radical as specified above, it is recommended to carry out:

the addition of an orthoformate to the amino functional group of an aminofurazan of formula (Ma) (by successive reaction with, for example, methyl orthoformate and sodium azide).

Route A, the chemical reaction mentioned above, has been represented diagrammatically in the reaction scheme presented below.

For the preparation of a compound of formula (I) in which Het is a triazolyl radical as specified above, it is recommended to carry out:

the diazotization with NaNO$_2$, in concentrated acid medium, of an aminofurazan of formula (IIIa), followed by:

for the preparation of a 4-(5-nitro-1,2,3-triazol-2-yl)furazan (route B below):

the condensation of the diazonium salt obtained with nitroacetaldoxime;

the dehydration of the product obtained in the presence of an inorganic or organic anhydride, in particular in the presence of acetic anhydride (cyclization);

for the preparation of a 4-(4-nitro-1,2,3-triazol-1-yl)furazan (route C below):

the reaction of the diazonium salt obtained with sodium azide, in order to obtain an azidofurazan of formula in which R is as defined above;

(IIIb) the cycloaddition of said azidofurazan with morpholinonitro-ethene.

The two series of chemical reactions above (including route B or route C) have been represented diagrammatically in the reaction scheme represented below.

The nitro substituent of the heterocycle concerned (Het=triazolyl radical) has scarcely any effect on the implementation of the reactions.

The two routes (routes B and C) involve the same intermediate (the diazonium salt of the starting aminofurazan). Depending on the route chosen (B or C), the connection with the furazan nucleus can be made: either via the central nitrogen (2) (route B), or via the nitrogen (1) of the 4-nitro-1,2,3-triazolyl ring (route C).

The conditions of Licht and Ritter (*J. Energ. Mat.*, 1994, 12, 223-35) employing nitroacetaldoxime result in the formation of a furazan-heterocycle bond via the central nitrogen (2) of the 4-nitro-1,2,3-triazole ring. The second route, which consists in reacting the azidofurazan intermediate and morpholinonitroethene (Batog et al., Chemistry of *Heterocyclic Compounds*, 2000, 36, 343), results in the formation of a furazan-heterocycle bond via the nitrogen (1) of the 4-nitro-1,2,3-triazole ring.

The implementation of route B above is illustrated in example 3 below.

As regards route C above, it can obviously be limited to the cycloaddition of the azidofurazan with morpholinonitroethene, if said azidofurazan is available. Said azidofurazan can in fact consist of a known compound (when R represents a nitro, nitroazofurazanyl or nitroazooxylfurazanyl radical). This condensation stage is illustrated in example 5 below.

A more effective method for the preparation of a compound of formula (I) in which and Het=the 1,2,3,4-tetrazol-1-yl radical, the 4-(4-nitro-1,2,3-triazol-1-yl) radical or the 4-(5-nitro-1,2,3-triazol-2-yl) radical is also provided.

Said method comprises the use of the above reactions, route A, diazotization+route B or diazotization+route C, starting from a hydroxyfurazan of formula (IVa):

in order to obtain said hydroxyfurazan functionalized by an azole, followed by the reaction, in basic medium, of said functionalized hydroxyfurazan with dinitrofurazanyl ether.

The latter method can be represented diagrammatically as follows, in a context where route B has been followed to produce the functionalized hydroxyfurazan:

Asymmetric ethers are thus "directly" accessed. The transetherification reaction concerned has been described in particular by A. B. Scheremetev in *Russ. Chem. Bull. Int. Ed.* 2002, 51, 659. It now consists in reacting dinitrofurazanyl ether and a hydroxyfurazan functionalized beforehand by the desired nitroazolyl or tetrazolyl radical.

This method has been illustrated in example 4 below.

Furthermore, it is possible to obtain some compounds of the invention from other compounds of the invention (different in the nature of the R substituent).

Thus, in the context of the second subject matter of the present invention, it is also possible to obtain:

a compound of formula (I) in which:

and Het is as defined above (generally), by reducing, under mild conditions, the corresponding compound (same Het) of formula (I) in which:

a compound of formula (I) in which:

and Het is as defined above (generally), by hydrolyzing the corresponding compound of formula (I) in which R=—NO$_2$, in order to obtain the hydroxyfurazan of formula (I'):

(I')

and by then reacting, in basic medium, said hydroxyfurazan with dinitrofurazanyl ether. The reaction scheme concerned is shown below:

It might complement the scheme on page 8. Its second stage is analogous to that mentioned above.

The compounds of formula (I) (novel compounds of the invention+3-nitro-4-(4-nitro-1,2,3-triazol-1-yl)furazan) as identified above, generally, indeed even specifically, as capable of being obtained by the processes described above, exhibit characteristics which are entirely exceptional in terms of stability and vulnerability. Their performance characteristics for propellant and explosive applications are advantageous. They clearly constitute advantageous competitors with regard to current conventional energetic molecules of nitramine type, such as octogen (HMX) or CL20 (hexanitrohexaazaisowurtzitane).

According to its third subject matter, the present invention thus relates to energetic compositions including (an effective amount of) at least one compound chosen from those of formula (I) (those of the invention, as described above, and 3-nitro-4-(4-nitro-1,2,3-triazol-1-yl)furazan).

The determination of the effective amount is within the scope of a person skilled in the art, in the light of the exact outlet desired for said energetic compositions. Said energetic compositions can consist in particular of explosive compositions or propellant compositions. These two types of energetic compositions (with conventional energetic molecules) are familiar to a person skilled in the art.

The energetic compositions of the invention of the first type (explosive compositions) include or do not include a binder (inert or energetic). They are generally composed to at least 20% by weight (advantageously to at least 50% by weight) of at least one compound chosen from those of the invention of formula (I) and 3-nitro-4-(4-nitro-1,2,3-triazol-1-yl)furazan, very generally composed to at least 20% by weight (advantageously to at least 50% by weight) of such a compound chosen from those of the invention of formula (I) and 3-nitro-4-(4-nitro-1,2,3-triazol-1-yl)furazan. They are entirely capable of being composed to more than 95% by weight, indeed even to 100% by weight, of at least one compound chosen from those of formula (I) (those of the invention+3-nitro-4-(4-nitro-1,2,3-triazol-1-yl)furazan).

Incidentally, it may be noted here that some of the compounds of the invention have an obvious potential to participate in insensitive explosive compositions of MURAT type (MURAT for MUnition with Risk ATtenuation) as replacement for RDX (hexogen=cyclomethylenetrinitramine).

The energetic compositions of the invention of the second type (propellant compositions) include a neutral or energetic binder. They generally include at most 80% by weight (advantageously between 50 and 80% by weight) of at least one compound chosen from those of the invention of formula (I) and 3-nitro-4-(4-nitro-1,2,3-triazol-1-yl)furazan, very generally at most 80% by weight (advantageously between 50 and 80% by weight) of a compound chosen from those of the invention of formula (I) and 3-nitro-4-(4-nitro-1,2,3-triazol-1-yl)furazan.

The intention is now to illustrate the invention by the examples below.

Six compounds of formula (I) have been prepared (see table 1 below).

Attention has been directed at their properties and performance characteristics (see tables 2 and 3 below).

EXAMPLE 1

5 ml of anhydrous acetonitrile are placed in a dry three-necked flask under argon, 32.6 mg (1.358 mmol) of NaH are then added, followed by 154 mg (1.35 mmol) of 3-nitro-1,2,4-triazole, and the mixture is stirred at ambient temperature for 15 minutes in order to complete the formation of the nitrotriazolate anion. Dinitrofurazanyl ether is added all at once (300 mg, 1.23 mmol) and then the medium is stirred at ambient temperature for 20 hours. 20 ml of water are subsequently added. The product is extracted with chloroform and the chloroform extract is dried over magnesium sulfate, filtered and then evaporated. The product is purified on silica gel. 194 mg of pure product are thus isolated (yield 63%).

The expanded formula of said product and also results of physicochemical ($^1$H, $^{13}$C and $^{14}$N NMR) analyses confirming its structure appear in the first column of table 1 below.

EXAMPLE 2

5 ml of anhydrous acetonitrile are placed in a dry three-necked flask under argon and then 165.4 mg (1.03 mmol) of dinitrofurazan are added, followed by 117.1 mg (1.008 mmol) of 3-nitro-1,2,4-triazole. 3 ml of a solution of pyridine (92 mg) diluted in acetonitrile are added dropwise to the reaction medium at 20° C. The medium is stirred at ambient temperature for 5 hours. 20 ml of water are subsequently added. The product is extracted with chloroform and the chloroform extract is dried over magnesium sulfate, filtered and then evaporated. The product is purified with silica gel. 56 mg of pure product are thus isolated (yield 24%, with respect to the dinitrofurazan).

The product obtained is the same as that obtained in example 1 (see the first column of table 1 below).

EXAMPLE 3

2.05 g of aminonitrofurazan (15 mmol) are added, between 0 and 5° C., to a solution of concentrated sulphuric acid (12 ml) and concentrated phosphoric acid (12 ml). Sodium nitrite (1.10 g, 15.8 mmol) is added in small portions. 1.64 g of nitroacetaldoxime are added all at once to the reaction medium. The reaction medium is left to stir for one hour and is then run onto 40 g of ice. Separation by settling is allowed to take place for a few hours and then the intermediate is filtered off, rinsed with water and then dried over $P_2O_5$. 0.46 g of dry product obtained beforehand is placed in 15 ml of distilled water. 0.75 ml of acetic anhydride is run in slowly at 20° C. while maintaining the pH at 7 by addition of 5% sodium hydroxide. At the end of the addition, the medium is acidified using a 10% HCl solution. The product is extracted with ethyl acetate and the ethyl acetate extract is dried over magnesium sulfate, filtered and then evaporated. The product is purified on silica gel. 72 mg of pure product are thus isolated (yield 2%).

The expanded formula of the said product and also results of physicochemical $^1$H, $^{13}$C and $^{14}$N NMR) analyses confirming its structure appear in the second column of table 1 below.

EXAMPLE 4

3-Hydroxy-4-(4-nitro-1,2,3-triazol-2-yl)furazan is prepared from aminohydroxyfurazan by adopting the same procedure described in example 3 above. 5 ml of anhydrous acetonitrile are placed in a dry three-necked flask under argon and then 264.7 mg (1.34 mmol) of 3-hydroxy-4-(4-nitro-1,2,3-triazol-2-yl)furazan are added, followed by 39 mg (1.62 mmol) of sodium hydride. The medium is heated to 40° C. and then dinitrofurazanyl ether (323 mg) is rapidly added thereto. The medium is stirred at reflux for 6 hours. 20 ml of chloroform are subsequently added. The salts which precipitate are filtered off. The medium is concentrated under vacuum and then the product is purified on silica gel. 170 mg of pure product are thus isolated (yield 56%).

The expanded formula of said product and also results of physicochemical ($^1$H, $^{13}$C and $^{14}$N NMR) analyses confirming its structure appear in the third column of table 1 below.

EXAMPLE 5

0.5 g of azidonitroazoxyfurazan (1.87 mmol) is introduced into 10 ml of dioxane in the presence of 0.22 g of sulphuric acid. 0.35 g of morpholinonitroethene is subsequently added. The mixture is heated at 80° C. for 2 hours and then evaporated to dryness. The crude product is purified on silica gel. 60 mg of pure product are thus isolated (yield 9.5%).

The expanded formula of said product and also results of physicochemical ($^1$H, $^{13}$C and $^{14}$N NMR) analyses confirming its structure appear in the fourth column of table 1 below.

EXAMPLE 6

20 ml of anhydrous acetonitrile are placed in a dry three-necked flask under argon and then 600 mg of dinitrofurazan (3.75 mmol) are added, followed by 592 mg (3.75 mmol) of 3,4-dinitropyrazole. 10 ml of a solution of pyridine (296 mg, 3.75 mmol) diluted in acetonitrile are added dropwise to the reaction medium at 20° C. The medium is stirred at ambient temperature for 5 hours. 20 ml of water are subsequently added. The product is extracted with chloroform and the chloroform extract is dried over magnesium sulfate, filtered and then evaporated. The product is purified on silica gel. 300 mg of pure product are thus isolated (yield 30%).

The expanded formula of said product and also results of physicochemical ($^1$H, $^{13}$C and $^{14}$N NMR) analyses confirming its structure appear in the fifth column of table 1 below.

EXAMPLE 7

20 ml of anhydrous acetonitrile are placed in a dry three-necked flask under argon and then 463 mg of dinitrofurazanyl ether (1.90 mmol) are added, followed by 300 mg (1.90 mmol) of 3,5-dinitropyrazole. 10 ml of the solution of pyridine (150 mg, 1.90 mmol) diluted in acetonitrile are added dropwise to the reaction medium at 20° C. The medium is stirred at ambient temperature for 3 days. 20 ml of water are subsequently added. The product is extracted with chloroform and the chloroform extract is dried over magnesium sulfate, filtered and then evaporated. The product is purified on silica gel. 45 mg of pure product are thus isolated (yield 8.7%).

The expanded formula of the said product and also results of physicochemical ($^1$H, $^{13}$C and $^{14}$N NMR) analyses confirming its structure appear in the sixth column of table 1 below.

Said table 1 is provided below.

TABLE 1

| Example | 1, 2 | 3 | 4 |
|---|---|---|---|
| Formula | [structure] | [structure] | [structure] |
| $^1$H NMR (ppm) | 9.47 | 8.60 | 8.56 |
| $^{13}$C NMR (ppm) | 146.1, 150.6, 156.6 (t), 165.1 (broad) | 134.7 (CH), 145.2 (Q), 153.4 (t, C—NO$_2$, $J_{C-N}$ = 19.7 Hz), 156.3 (C—NO$_2$, broad) | 134.3 (CH), 143.6, 151.2, 153.9, 154.6, 155.4 |
| $^{14}$N NMR (ppm) | 343.5, 351.9 | 340.4 (NO$_2$), 349.3 (NO$_2$) | 349.3, 341.3, 311.1 |
| MS | EI: 227 (M$^{+\cdot}$), CI$^+$ (CH$_4$): 228 (MH$^+$) | EI: 227, 181 (M-NO$_2$)$^+$; CI$^{+\cdot}$ 228 (MH)$^+$; CI$^-$: 226 (M − H)$^-$ | EI: 311 (M)$^{+\cdot}$, CI$^+$ (NH$_3$): 311, Liquid infusion: 312 (MH)$^+$, 324 (MHNa$^+$) |

| Example | 5 | 6 | 7 |
|---|---|---|---|
| Formula | [structure] | [structure] | [structure] |
| $^1$H NMR (ppm) | | 9.72 | 9.62 (s, CH) | 8.49 (s, CH) |
| $^{13}$C NMR (ppm) | 154.9, 153.6, 152.1, 149.9, 148.3, 126.4 | 130.2, 137.3, 147.4, 151.1, 156.3 | 105.4, 147.0, 148.7, 157.0, 157.9 |
| $^{14}$N NMR (ppm) | 353.7, 341.2, 310.4 | 343.6, 352.6 | 353.4, 348.3, 343.2, 310.6 |

TABLE 1-continued

| | | | |
|---|---|---|---|
| MS | CI+ (CH4) 340 (MH)+, 329, 368 | EI: 271 (25) [M]+· | CI+ (CH4): 272 (100) [MH]+, 300 (13) [M + C2H5]+, 312 (5) [M + C3H5]+ |

Figure 1:
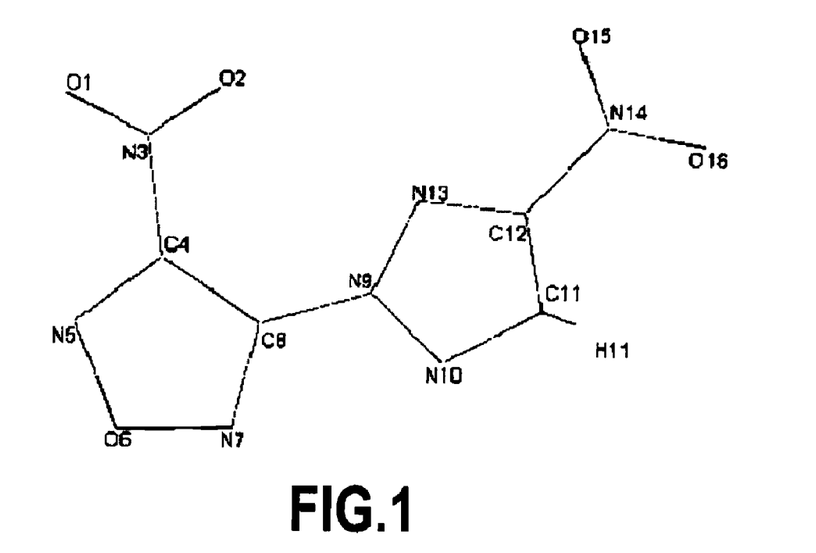
FIG. 1 shows the structure of the product of example 3, as obtained by X-ray diffraction.
Figure 2:
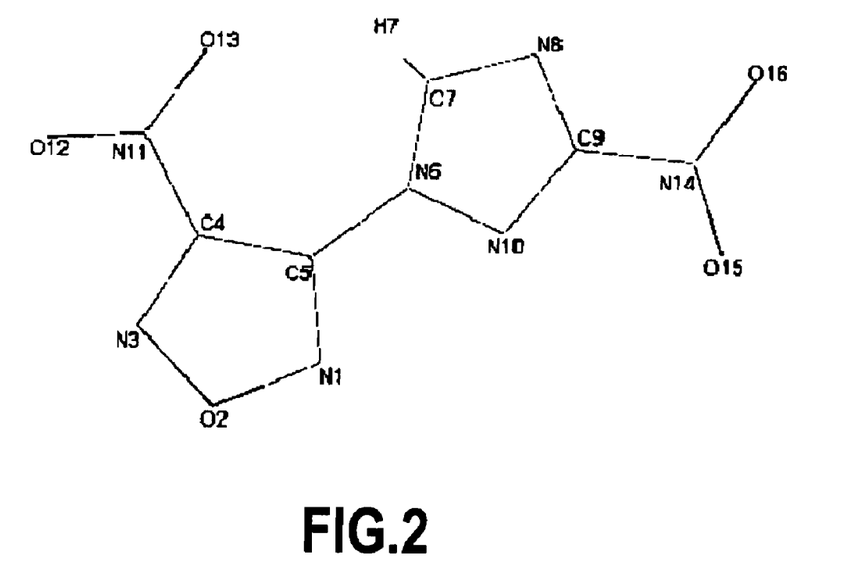
FIG. 2 shows the structure of the product examples 1 and 2, as obtained by X-ray diffraction.

Furthermore, the structures of the products obtained in examples:
1 and 2: 3-nitro-4-(3-nitro-1,2,4-triazol-1-yl)furazan and
3: 3-nitro-4-(4-nitro-1,2,3-triazol-2-yl)furazan
were confirmed by X-ray diffraction.

The results obtained are shown respectively in the appended FIGS. 2 and 1.

Attention has been directed at the properties and performance characteristics of the products (compounds) of the invention prepared in examples 1 to 7 above.

a) Sensitivity and Thermal Stability

The sensitivities of the products of the invention and, for comparison, those of HMX and HNIW (HMX=octogen, HNIW=CL20=hexanitrohexaazaisowurtzitane), were assessed with regard to external attacks of mechanical and electrostatic type by impact, friction and electric spark tests.

The tests carried out are presented below.

Impact sensitivity: The test carried out corresponds to that described in the standard NF T 70-500, itself similar to the UNO test 3a)ii) resulting from the "Recommendations on the Transport of Dangerous Goods—Manual of Tests and Criteria, Fourth revised edition, ST/SG/AC.10/11/Rev.4, ISBN 92-1-239083-8ISSN 1014-7179". The energy producing 50% (Bruceton method of treatment of the results) of positive results for an explosive material subjected to the impacts of a weight is determined by a minimum series of 30 trials. The test material is confined in a steel device composed of two rollers and a guide ring. By modifying the mass and the drop height of the weight, it is possible to vary the energy from 1 to 50 J. Due to the small amount of material available for some of the products tested, only a reduced number of reproducibility tests were carried out for said products, in comparison with the recommendations of the standard NF T 70-500.

Friction sensitivity: The test carried out corresponds to that described in the standard NF T 70-503, itself similar to the UNO 3b)ii) test. The force producing 50% of positive results for an explosive material subjected to friction is determined by a minimum series of 30 trials using the Bruceton method. The test material is placed on a porcelain plate of defined roughness, driven with only a to-and-fro movement with an amplitude of 10 mm at the rate of 7 cm/s offload, with respect to a porcelain peg resting on the material. The force applied to the porcelain peg which is supported on the material can vary from 7.8 to 353 N. Due to the small amount of material available for some of the products tested, only a reduced number of reproducibility tests were carried out for said products, with respect to the recommendations of the standard NF T 70-503.

Sensitivity to electric spark ignition: The test carried out is a test developed by the Applicant Company without NF or UNO equivalent. The test material, placed in a dish with a diameter of 10 mm and a height of 1.5 mm, is positioned between two electrodes and is subjected to an electric spark of variable energy from 5 to 726 mJ. It is observed whether or not a pyrotechnic event has occurred and the energy threshold at which the material no longer ignites is determined. This value is confirmed by 20 successive trials. Due to the small amount of material available for some of the products tested, only a reduced number of reproducibility tests were carried out for said products.

The thermal stability for its part was determined as follows.

Thermal stability: the thermal stability is analyzed by the Differential Thermal Analysis (DTA or DSC) method. Differential thermal analysis (DTA) consists in characterizing a product in a given temperature range by studying the exchange of heat in the conversions and reactions which it undergoes whenever it is subjected to a rise in temperature. The transition temperatures are detected by modification of the heat flow used to heat the sample. The method makes it possible to distinguish the melting point (m.p.), the boiling point (b.p.) and the decomposition point (dec.).

The results obtained are given in table 2 below.

TABLE 2

| Compounds | Sensitivity | | | Thermal stability |
|---|---|---|---|---|
| | Impact | Friction | Electric spark | |
| HMX | 4 J | 125 | >726 mJ | |
| HNIW | 2 J | 75 | 56-726* | dec. 223° C. (onset) |
| EX. 1 and 2 | 5.1 J | 353 N | insensitive | m.p. 152.8° C. dec. 240-371° C. |
| EX. 3 | 13 J | >353 N | insensitive | m.p. 50.3° C. b.p. 215° C. |
| EX. 4 | >3.16 J | >353 N | insensitive | m.p. 80.9° C. b.p. 198° C. |
| EX. 5 | 1 J | 30 N | <51 mJ | m.p. 150° C. dec. 191° C. (onset) |
| EX. 6 | >3.16 J | >353 N | >104 mJ | m.p. 98.0° C. b.p. 276° C. |
| EX. 7 | >3.16 J | >353 N | >104 mJ | m.p. 144.8° C. b.p. 239° C. |

*depending on the particle size of the product
m.p. = melting point
b.p. = boiling point
dec. = decomposition Consideration of the values shown in said table 2 calls for the following comments:

The compounds of the invention exhibit relatively low sensitivities in the various tests. It is noted that the sensitivity of the ether (compound of example 4) is of the same level as that of the monofurazans (compounds of examples 1, 2, 3, 6 and 7). The sensitivity of the azoxy derivative (compound of example 5) appears greater than that of the other furazans. It is also noted that several of the compounds of the invention (not the azoxy derivative of said example 5) are insensitive to friction, in the same way as "insensitive" molecules of the prior art well known to a person skilled in the art: NTO (5-nitro-1,2,4-triazolone) and TATB (1,3,5-triamino-2,4,6-trinitrobenzene).

The compounds of the invention exhibit very high thermal stabilities. These novel furazans are observed to decompose in the vicinity of 200° C. In several cases, the energetic products melt and then vaporize subsequent to the rise in the temperature without initiating the least decomposition. This is evidence of exceptional thermal stability of said compounds.

b) Performance Characteristics

The energy level of the products of the invention was determined by calculation from their density and their enthalpy of formation.

The performance characteristics were then calculated in explosion and then in propulsion, for applications as simple propellants (0% ammonium perchlorate and 0% aluminum), in the presence of binders plasticized with nitrated oils. The constituent polymers of said binders are of energetic type (poly(glycidyl azide): PGA) or inert type of polyether type (HTPE=hydroxytelechelic polyether). The ratio used for the prediction of the propellant performance characteristics is 85/15 (charge/binder). For the explosives and propellants, the references are octogen (HMX) and ε-hexanitrohexaazaisowurtzitane (ε-CL-20=ε-HNIW).

The results are shown in table 3 below.

TABLE 3

| Compounds | Enthalpy of formation (kcal/mol) | Density | Explosive Energy (V/Vo = 2)* | Simple propellant Charge/PGA (85/15) SI (s) | Simple propellant Charge/HTPE (85/15) SI (s) |
|---|---|---|---|---|---|
| HMX | 20.1 | 1.908 | 100% HMX | 260.4 | 249.9 |
| EX. 1 and 2 | 123.3 | 1.884 | 102% HMX | 264.6 | 253.8 |
| EX. 3 | 158.5 | 1.884 | 111% HMX | 276.3 | 267.2 |
| EX. 4 | 209.4 | 1.921 | 112% HMX | 273.2 | 263.2 |
| EX. 5 | 272.4 | 1.954 | 120% HMX | 278.7 | 269.4 |
| EX. 6 | 124.1 | 1.934 | 110% HMX | 270.5 | 261.8 |
| EX. 7 | 124.1 | 1.936 | 110% HMX | 270.5 | 261.8 |
| ε-CL20 | 91.5 | 2.04 | 120% HMX | 268.0 | 260.1 |

*Detonation energy released, kinetic and internal, for a degree of expansion of the products to twice their starting volume.

Said results clearly demonstrate the advantage of the compounds of the invention.

The invention claimed is:

1. A compound of formula (I)

in which:

and Het is an azolyl radical chosen from nitroazolyl and tetrazolyl radicals;

with the exception of 3-nitro-4-(4-nitro-1,2,3-triazol-1-yl)furazan.

2. The compound as claimed in claim 1, of formula (I) in which Het is an azolyl radical chosen from unsubstituted (bi)tetrazolyl radicals and (bi)pyrrolyl, (bi)pyrazolyl, (bi)triazolyl and (bi)tetrazolyl radicals substituted by at least one nitro group.

3. The compound as claimed in claim 1, of formula (I) in which Het is chosen from nitrotriazolyl; dinitrotriazolyl; dinitropyrazolyl; tetrazolyl; 5-nitrotetrazolyl; bi(nitropyrrolyl); bitetrazolyl; bi(nitrotriazolyl) and bi(dinitropyrazolyl) radicals.

4. The compound as claimed in claim 1, of formula (I) in which Het is chosen from the following radicals:
3-nitro-1,2,4-triazol-1-yl,
4-nitro-1,2,3-triazol-2-yl,
4-nitro-1,2,3-triazol-1-yl,
3,4-dinitropyrazolyl,
3,5-dinitropyrazolyl, and
1,2,3,4-tetrazol-1-yl.

5. The compound as claimed in claim 1, of formula (I), chosen from:
3-nitro-4-(3-nitro-1,2,4-triazol-1-yl)furazan,
3-nitro-4-(4-nitro-1,2,3-triazol-2-yl)furazan,
4-nitro-4'-(4-nitro-1,2,3-triazol-2-yl)bisfurazanyl ether,
4-nitro-4'-(4-nitro-1,2,3-triazol-1-yl)-3,3'-azoxybisfurazan,
3-nitro-4-(3,4-dinitropyrazolyl)furazan, and
3-nitro-4-(3,5-dinitropyrazolyl)furazan.

6. An energetic composition, comprising an effective amount of at least one compound chosen from the compounds of formula (I) as claimed in claim 1 and 3-nitro-4-(4-nitro-1,2,3-triazol-1-yl)furazan.

7. The energetic composition as claimed in claim 6, which comprises at least 20% by weight of at least one compound chosen from the compounds of formula (I) and 3-nitro-4-(4-nitro-1,2,3-triazol-1-yl)furazan.

8. The energetic composition as claimed in claim 6, which comprises at most 80% by weight of at least one compound chosen from the compounds of formula (I) and 3-nitro-4-(4-nitro-1,2,3-triazol-1-yl)furazan in a binder.

* * * * *

UNITED STATES PATENT AND TRADEMARK OFFICE
CERTIFICATE OF CORRECTION

PATENT NO. : 8,211,252 B2
APPLICATION NO. : 12/521680
DATED : July 3, 2012
INVENTOR(S) : Jacob et al.

Page 1 of 1

It is certified that error appears in the above-identified patent and that said Letters Patent is hereby corrected as shown below:

Cover Page, item (73) Assignee: HERAKLES, Le Haillan (FR) should be added.

Signed and Sealed this
Fourth Day of September, 2012

David J. Kappos
*Director of the United States Patent and Trademark Office*